(12) United States Patent
Oren et al.

(10) Patent No.: US 8,617,219 B2
(45) Date of Patent: Dec. 31, 2013

(54) ARTHROSCOPIC BONE TRANSPLANTING PROCEDURE, AND MEDICAL INSTRUMENTS USEFUL THEREIN

(75) Inventors: Ran Oren, Doar-Na Oshrat (IL); Laurent Lafosse, Annecy-Le-Vieux (FR); Shai Nahmias, Nahariya (IL); Dan Moor, Doar-Na Oshrat (IL)

(73) Assignee: T.A.G. Medical Devices—Agriculture Cooperative Ltd., Kibbutz Gaaton (IL)

(*) Notice: Subject to any disclaimer, the term of this patent is extended or adjusted under 35 U.S.C. 154(b) by 806 days.

(21) Appl. No.: 12/375,422

(22) PCT Filed: Jul. 30, 2007

(86) PCT No.: PCT/IL2007/000952
§ 371 (c)(1),
(2), (4) Date: Nov. 6, 2009

(87) PCT Pub. No.: WO2008/015670
PCT Pub. Date: Feb. 7, 2008

(65) Prior Publication Data
US 2010/0069974 A1    Mar. 18, 2010

Related U.S. Application Data

(60) Provisional application No. 60/834,173, filed on Jul. 31, 2006.

(51) Int. Cl.
*A61B 17/70* (2006.01)
*A61B 17/88* (2006.01)

(52) U.S. Cl.
USPC ........................................ 606/279; 606/247

(58) Field of Classification Search
USPC .................................................. 606/247, 279
See application file for complete search history.

(56) References Cited

U.S. PATENT DOCUMENTS

| | | | |
|---|---|---|---|
| 5,562,686 A | 10/1996 | Sauer et al. | |
| 5,792,152 A | 8/1998 | Klein et al. | |
| 5,961,530 A | 10/1999 | Moore et al. | |
| 5,993,466 A | 11/1999 | Yoon | |
| 6,015,411 A | 1/2000 | Ohkoshi et al. | |
| 6,045,555 A | 4/2000 | Smith et al. | |
| 2002/0065526 A1 | 5/2002 | Oren et al. | |
| 2002/0099385 A1 | 7/2002 | Ralph et al. | |
| 2004/0122435 A1 | 6/2004 | Green et al. | |
| 2006/0167475 A1 | 7/2006 | Bischof et al. | |
| 2007/0073342 A1 | 3/2007 | Stone et al. | |

FOREIGN PATENT DOCUMENTS

| | | |
|---|---|---|
| DE | 29805703 | 8/1998 |
| EP | 0686375 | 12/1995 |
| EP | 0880938 | 12/1998 |

(Continued)

OTHER PUBLICATIONS

Communication Relating to the Results of the Partial International Search Dated Dec. 12, 2007 From the International Searching Authority Re.: Application No. PCT/IL2007/000952.

(Continued)

*Primary Examiner* — Sameh Boles

(57) ABSTRACT

Described is an arthroscopic bone transplanting procedure for transplanting a section of a first bone to a second bone. The described procedure is particularly useful for the treatment an anterior shoulder instability, where the first bone is the coracoid and the second bone is the glenoid. Also described is a kit of medical instruments particularly useful in such a procedure.

18 Claims, 6 Drawing Sheets

(56) References Cited

FOREIGN PATENT DOCUMENTS

| | | |
|---|---|---|
| EP | 1488747 | 12/2004 |
| FR | 2560764 | 9/1985 |
| JP | 10-508780 | 9/1998 |
| JP | 11-047175 | 2/1999 |
| JP | 2002-102236 | 4/2002 |
| JP | 2002-511301 | 4/2002 |
| RU | 2087133 | 8/1997 |
| WO | WO 96/15727 | 5/1996 |
| WO | WO 99/52453 | 10/1999 |
| WO | WO 2007/002432 | 11/2007 |
| WO | WO 2008/015670 | 2/2008 |
| WO | WO 2008/146291 | 12/2008 |

OTHER PUBLICATIONS

International Preliminary Report on Patentability Dated Feb. 3, 2009 From the International Bureau of WIPO Re.: Application No. PCT/IL2007/000952.
International Search Report Dated Apr. 15, 2008 From the International Searching Authority Re.: Application No. PCT/IL2007/000952.
International Search Report Dated Mar. 26, 2009 From the International Searching Authority Re.: Application No. PCT/IL08/00731.
Written Opinion Dated Apr. 15, 2008 From the International Searching Authority Re.: Application No. PCT/IL2007/000952.
Written Opinion Dated Mar. 26, 2009 From the International Searching Authority Re.: Application No. PCT/IL08/00731.
International Preliminary Report on Patentability Dated Jan. 21, 2010 From the International Bureau of WIPO Re.: Application No. PCT/IL2008/000731.
Official Action Dated Jun. 19, 2013 From the US Patent and Trademark Office Re. U.S. Appl. No. 12/602,101.
Official Action Dated Sep. 19, 2012 From the US Patent and Trademark Office Re. U.S. Appl. No. 12/602,101.
Examiner's Report Dated Apr. 4, 2012 From the Australian Government, IP Australia Re. Application No. 2007280012.
Translation of Notice of Reason for Rejection Dated Jun. 29, 2012 From the Japanese Patent Office Re. Application No. 2009-522415.
Patent Examination Report Dated Oct. 16, 2012 From the Australian Government, IP Australia Re. Application No. 2007280012.
Translation of Notice of Reason for Rejection Dated Nov. 2, 2012 From the Japanese Patent Office Re. Application No. 2010-509949.
Applicant-Initiated Interview Summary Dated Sep. 4, 2013 From the US Patent and Trademark Office Re. U.S. Appl. No. 12/602,101.
Notice of Allowance Dated Oct. 24, 2013 From the US Patent and Trademark Office Re. U.S. Appl. No. 12/602,101.
Requisition by the Examiner Dated Sep. 19, 2013 From the Canadian Intellectual Property Office Re. Application No. 2,660,292.

ARTHROSCOPIC BONE TRANSPLANTING PROCEDURE, AND MEDICAL INSTRUMENTS USEFUL THEREIN

RELATED APPLICATIONS

This application is a National Phase of PCT Patent Application No. PCT/IL2007/000952 having International filing date of Jul. 30, 2007, which claims the benefit of U.S. Provisional Patent Application No. 60/834,173 filed on Jul. 31, 2006. The contents of the above Applications are all incorporated herein by reference.

FIELD AND BACKGROUND OF THE INVENTION

The present invention relates to an arthroscopic bone transplanting procedure and to medical instruments useful in such a procedure as may be supplied in the form of a kit. The invention is particularly useful in the treatment of an anterior shoulder instability, where a section of the coracoid is transplanted to the glenoid, and is therefore described below with respect to said transplant.

The range of movements the human shoulder can make far exceeds any other joint in the body. The shoulder joint is a ball and socket joint, similar to the hip; however, the socket of the shoulder joint is extremely shallow, and thus inherently unstable. Muscles and tendons serve to keep the bones in approximation. In addition, in order to compensate for the shallow socket, the shoulder joint has a cuff of fibrous cartilage called a labrum that forms a cup for the head of the arm bone (humerus) to move within. This cuff of cartilage makes the shoulder joint much more stable, yet allows for a very wide range of movement. When the labrum of the shoulder joint is damaged, the stability of the shoulder joint is compromised, leading to subluxation and dislocation of the joint. Recurrent dislocations may cause damage to the bones of the joint—the humeral head and the glenoid. In particular, damage to the anterior-inferior part of the glenoid will cause a decrease in the area of contact with the humeral head.

When bone deficiencies associated with anterior shoulder instability are present, the prognostic factors for the success of soft tissue repair are poor. Current standards of success are predicated on the restoration of motion and strength and the return to full functional activities, including competitive athletics. Reestablishment of anterior shoulder stability requires the recognition and the treatment of osseous defects.

Several surgical procedures have been described for the management of osseous deficiencies in association with anterior shoulder instability, involving the transplantation of a portion of the coracoid process to the anterior-inferior section of the glenoid. The procedure described by Latarjet in 1954 involves the transplantation of a large section of the coracoid together with the conjoined tendon attached to it to reinforce the glenoid fossa and create an antero-inferior musculotendinous sling. The procedure has been performed since its disclosure with positive results as an open surgical intervention.

However, up to the present, no minimally invasive technique for performing it has been developed.

OBJECTS AND BRIEF SUMMARY OF THE PRESENT INVENTION

An object of the present invention is to provide an arthroscopic bone transplanting procedure which is particularly useful in the treatment of anterior shoulder instability, but may be used in other procedures involving implanting of a section of a first bone to a second bone. A further object of the invention is to provide instruments, which may be supplied in kit form, particularly useful in such an arthroscopic procedure.

According to one aspect of the present invention, there is provided an arthroscopic procedure for transplanting a section of a first bone to a second bone, comprising the following steps: (a) making small incisions to open portals for the introduction of medical instruments; (b) drilling a threaded bore in said section of said first bone; (c) attaching a first cannula to said section of said first bone; (d) separating said section from said first bone; (e) positioning said separated section of said first bone on said second bone; (f) replacing said first cannula by a second cannula attached to said separated bone section by a cannulated device; (g) introducing a guide wire through the cannulated device; (h) removing the cannulated device; (i) drilling a bore into the second bone by a cannulated drill guided by said guide wire; (j) removing the guide wire; (k) and applying a bone screw through said bore in said separated section of the first bone and said bore in said second bone.

The preferred embodiment of the invention described below is particularly useful for the treatment of anterior shoulder instability, or other disorders where it is desired to use at least two bone screws for attaching a section of a first bone to a second bone. When such a procedure is used, in step (b), two threaded bores at a fixed distance from each other are drilled in said section of the first bone; in step (c), the first cannula is a T-handle cannula and is attached in said first bore by sutures or flexible wires; in step (f), the second cannula is a double cannula and is attached to said section of the first bone by two cannulated devices; in step (g), two guide wires are introduced through the two cannulated devices, which cannulated devices are then removed in step (h); in step (i), two bores are drilled into the second bone by a cannulated drill guided by said guide wires; in step (j), the two guide wires are removed; and in step (k), two bone screws are applied through the two bones in the separated section of the first bone, and the two bores in the second bone.

Other aspects of the invention involve the construction of medical instruments, which may be supplied in a kit, particularly useful for the above-described bone transplanting procedures.

Further features of the invention will be apparent from the description below.

BRIEF DESCRIPTION OF THE DRAWINGS

The present invention is herein described below, the reference to the accompanying drawings, wherein:

FIGS. 3-20 illustrate various medical instruments, which may be supplied in kit form, particularly useful in an arthroscopic bone transplanting procedure for reconstructing the shoulder joint in accordance with the present invention, in which:

FIG. 3 shows a standard Kirschner wire;

FIG. 4 is a cannulated bone drill;

FIG. 5 shows a drill guide for drilling a second bore at a pre-determined distance from a first bore;

FIG. 6 is a thread tapping tool;

FIG. 8 shows a flexible wire;
FIG. 9 is a cannula with a T-handle;
FIG. 10 shows osteotomes, straight and curved;
FIG. 11 is a cannulator for a double cannula;
FIG. 12 is a double cannula;
FIG. 13 shows a suture hook;
FIG. 14 shows a cannulated device
FIG. 15 is a cannulated devicedriver;
FIG. 16 is a cannulated spike;
FIG. 18 shows cannulated bone drills;
FIG. 19 is a cannulated bone screw;
FIG. 20 is a screwdriver with a long cannulated shaft for the bone screws.

THE CONSTRUCTION OF THE SHOULDER JOINT

Figure 1A:
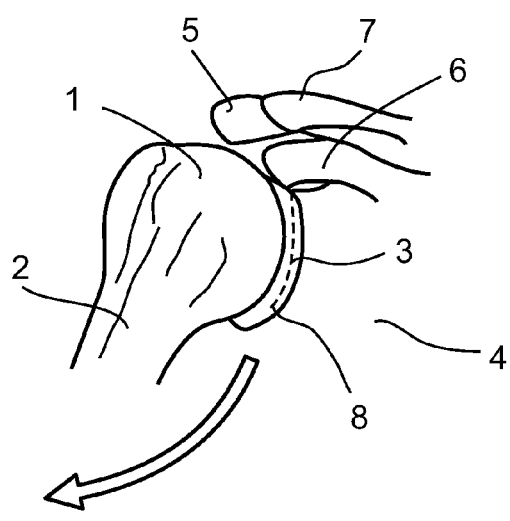
FIG. 1a is a schematic drawing of the gleno-humeral joint in the shoulder.

FIG. 1a illustrates the bones of the shoulder joint. The head 1 of the upper arm bone, the humerus 2, forms a ball-and-socket joint with the shallow glenoid cavity 3. The glenoid is the lateral part of the shoulder blade scapula 4. Two hook-like projections of the scapula seen overhanging the glenoid are the acromion 5 and the coracoid process 6. A group of muscles collectively know as the Rotator Cuff originate on the scapula and insert on the humerus. These serve to stabilize the joint by keeping the humeral head in contact with the glenoid cavity. The clavicle 7 connects the acromion to the breastbone sternum. The glenoid labrum 8, which is a flexible fibrous ligament, surrounds the glenoid rim enlarging its area of contact with the humerus. When dislocations in the direction shown by the arrow occur, the anterior-inferior part of the labrum is torn away from the glenoid, causing instability of the joint. Recurring dislocations may lead to osseous lesions.

Figure 1B:
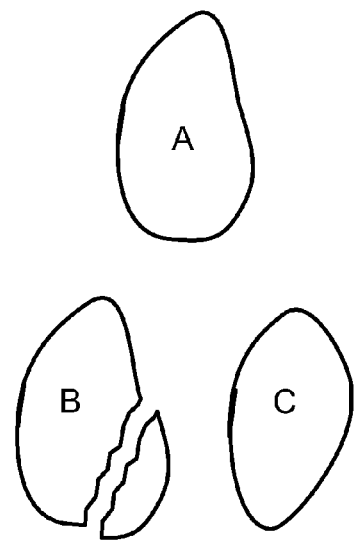
FIG. 1b is a schematic lateral view illustrating damage to the glenoid fossa.

FIG. 1b illustrates the type of damage to the glenoid socket caused by such dislocations. The pear-shape of the intact glenoid is shown at "A"; while bone loss at the inferior, wider section "A", caused by a dislocation, is shown at "B" and results in an inverted pear shape narrower lower section as shown at "C". This causes a partial loss of contact with the humeral head.

Figure 2A:
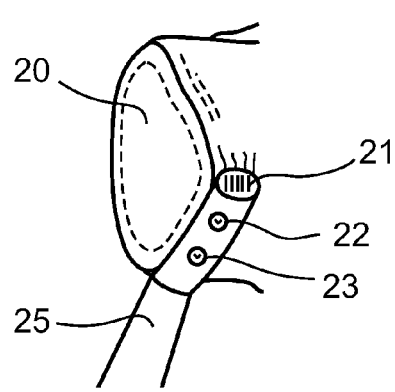
FIG. 2a is a schematic anterior view of the bone reconstruction.
Figure 2B:
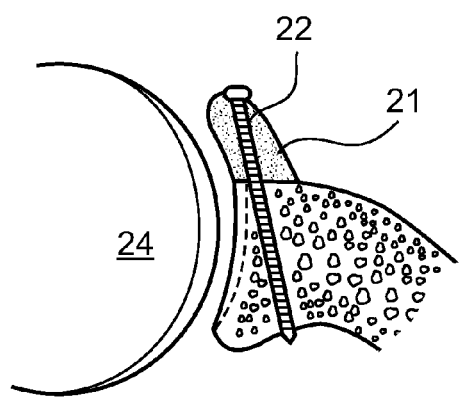
FIG. 2b is a transverse section through the reconstructed joint.
Figure 3:
Figure 4:
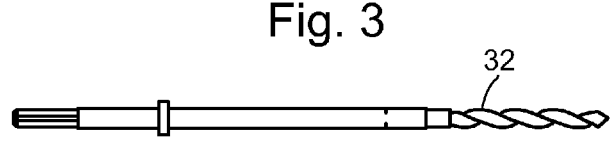

FIGS. 2a and 2b illustrate a bone reconstruction in accordance with the present invention.

DESCRIPTION OF A PREFERRED EMBODIMENT

The description below describes a kit of instruments, and the method of their use, for performing coracoid transfer (Latarjet procedure) arthroscopically. The kit consists of various instruments, including drills, drill guides, osteotomes, cannulae, suture manipulators, screws, screwdrivers and others, specific for the purpose of the method disclosed by the invention.

A Bone Transplantation Procedure and the Medical Instruments Used Therein

The procedure consists of the following main steps:
Opening portals (small incisions); introducing the arthroscope and instruments
Preparation of the coracoid and glenoid surfaces
Drilling and threading two holes in the coracoid at a fixed distance
Passing sutures or flexible wires through the holes
Attaching the coracoid by sutures or flexible wires to a cannula
Separating the section of the coracoid to be transferred
Positioning the graft on the glenoid
Attaching a double cannula to the coracoid with a cannulated device
Introducing K-wires through the cannulated device
Removing the cannulated device
Drilling into the glenoid with a cannulated drill over the K-wires
Attaching the transplanted coracoid onto the glenoid with bone screws
Removing the K-wires
Final fixing of the transplant (tightening the screws)
Removing the cannula.

Figure 20:

In the reconstruction of the shoulder joint according to the present invention illustrated in FIGS. 2a and 2b, 20 indicates the glenoid, 21 illustrates the coracoid graft implanted thereto by a pair of cannulated devices 22 and 23, 24 indicates the humeral head, and 25 indicates the conjoined tendon.

Figure 21:
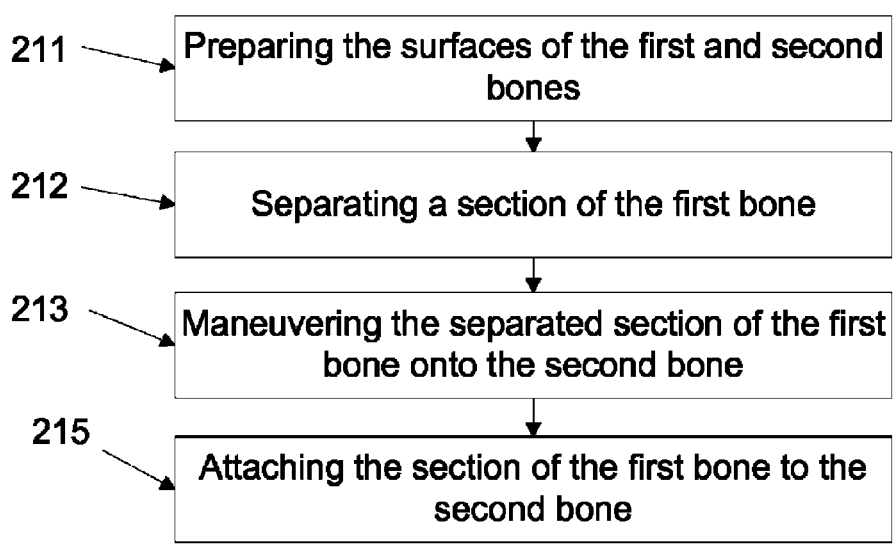
FIG. 21 is a flow diagram illustrating a preferred arthroscopic procedure in accordance with the present invention.

FIG. 21 shows the above described procedure divided into the following main building blocks, including:
preparing the surfaces of the first and second bones (211),
separating a section of the first bone (212),
maneuvering the separated section of the first bone onto the second bone (213), and
attaching the section of the first bone to the second bone (215).

A Bone Transplantation Procedure and the Medical Instruments Used Therein

FIGS. 3-20 illustrate the various medical instruments, preferably supplied in kit form, for performing an arthroscopic bone transplanting procedure in accordance with the present invention.

Portals (small incisions) are first made for introducing the arthroscope and instruments and for preparing the coracoid and glenoid surfaces, leaving the conjoined tendon (shown in FIG. 2b) attached to the coracoid. Two threaded holes are drilled in the coracoid process, using the bone drill shown at 32 in FIG. 4 with a diameter of about 3 mm. A Kirschner wire 31 (FIG. 3) is inserted at a safe distance from the lateral tip of the process for guiding the bone drill, and the first hole is drilled. For placing the second hole, the drill is inserted through the drill guide shown at 33 in FIG. 5. A guide pin 33a fixed at distance "d" from the center of the drill nut 33b ensures a predetermined distance of about 9 mm from the first hole. Both holes are threaded now with the elongated tap shown at 34 in FIG. 6. For safeguarding the integrity of the transplant, inserts may be implanted in the holes.

Figure 7A:
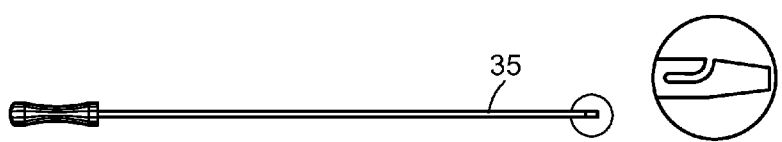
FIG. 7a is a suture loader.
Figure 7B:
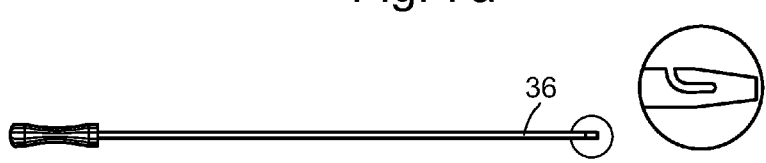
FIG. 7b is a suture retriever.
Figure 8:
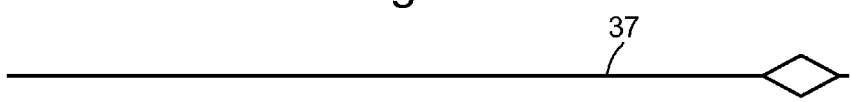
Figure 9:
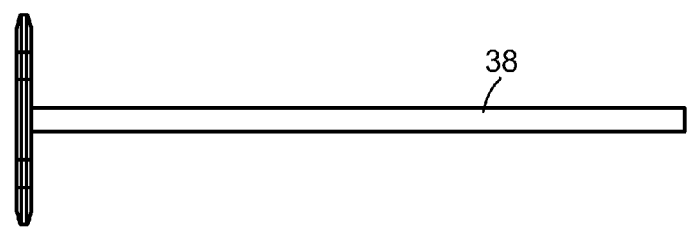
Figure 10:
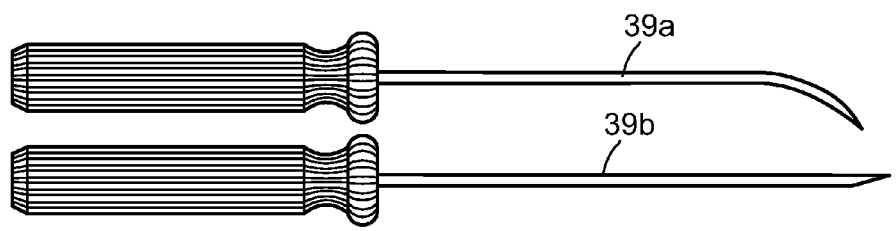

Suture strands or flexible wires are now attached to the coracoid process for securing during separation by threading them through the holes. A suture loader 35, FIG. 7a, and a suture retriever 36, in FIG. 7b are provided in the kit for manipulating the sutures. An alternative flexible wire 37 is shown in FIG. 8. The sutures/wires are drawn out through the shaft of a T-handle cannula shown at 38 in FIG. 9 and are fixed at the proximal, handle section of the cannula for holding the coracoid graft during separation and transfer to the receiving site. Osteotomes, such as those shown at 39a, 39b in FIG. 10, serve to separate the lateral section of the coracoid. At least one osteotome is provided in the kit.

Figure 11:
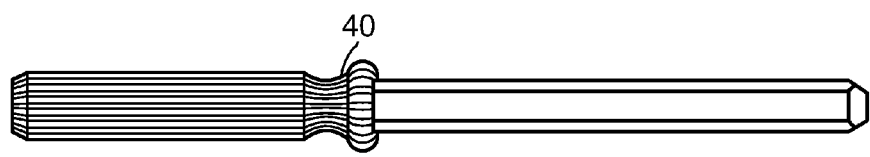
Figure 12:
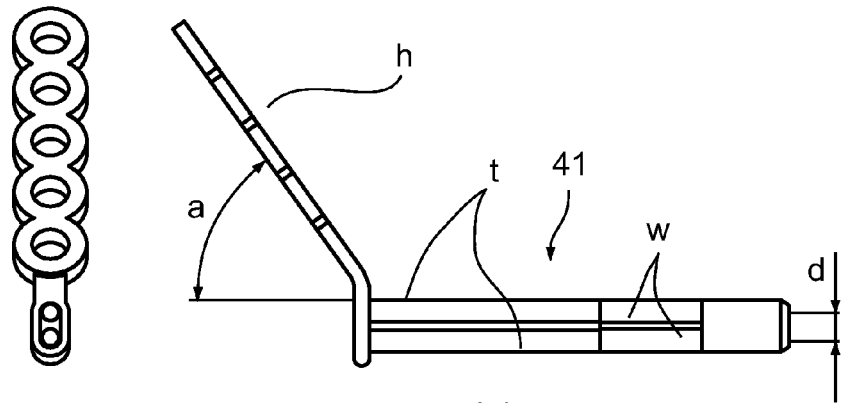
Figure 13:

Preparing for the transfer of the separated section of the coracoid, the subscapularis muscle is dissected and split to allow for transferring the T-handle cannula 38 with the coracoid transplant to the anterior-inferior, damaged section of the glenoid. The cannulator shown at 40 in FIG. 11 is used to dissect tissue and to free a passage to the receiving site. A double cannula shown at 41 in FIG. 12 is inserted through the passage freed by the cannulator.

Figure 5:
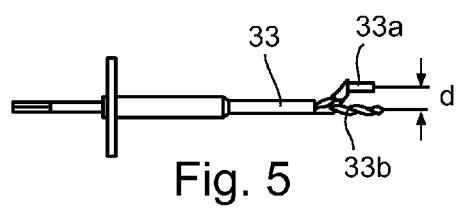
Figure 6:
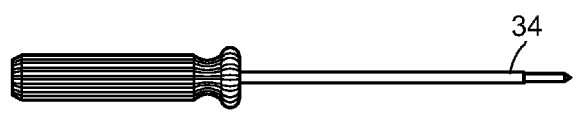

The two tubes "t" of the double cannula 41 are fixed, so that the distance of their centerlines "d" is identical to that of the drill guide 33 in FIG. 5. Handle "h" attached to the tube is offset at an angle "a" relative to the axis of the tubes and is formed to provide a firm grip. Angle "a" should be of an order of 40 to 65 degrees to allow maneuvering without obstructing the field of vision, and the length of the tubes measured from the handle should be about 150 mm. A window "w" is cut in each of the tubes near the distal end to enable observation of the interior of the two tubes, and the position of an instrument introduced into the tubes.

Figure 14:
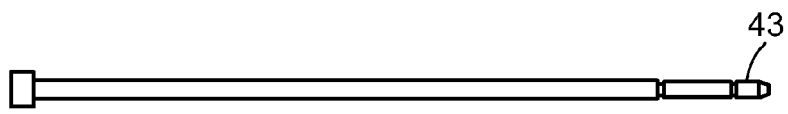
Figure 15:
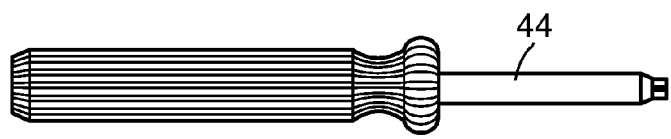
Figure 16:
Figure 17A:
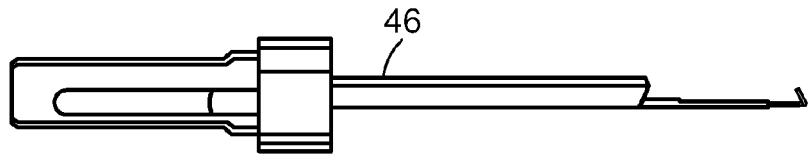
FIGS. 17a and 17b are side and top views, respectively, of a clamping device for holding a transplanted bone section to the receiving site.
Figure 17B:
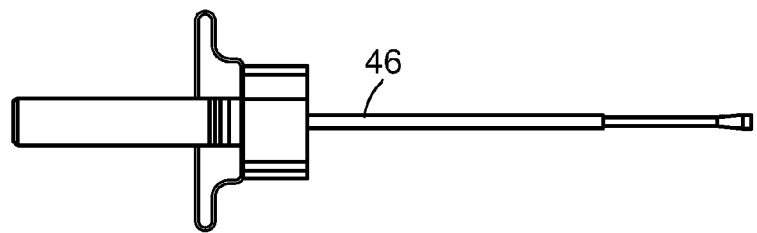
Figure 18:
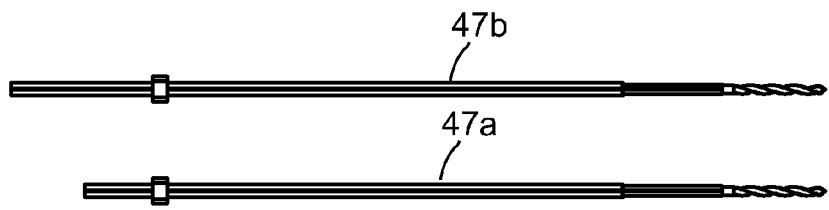

When the double cannula has been inserted to face the coracoid transplant, the T-handle cannula 38 is released from the sutures/wires attached to the graft and is withdrawn. Using a suture hook shown at 42 in FIG. 13, the sutures/wires are drawn through the tubes of the double cannula and an elongated cannulated holding device such as screws 43 shown in FIG. 14 are inserted over them into the tubes of the cannula. The screws are driven into the coracoid using a suitable instrument, such as the screw driver shown at 44 in FIG. 15 until the coracoid is firmly attached to the cannula. An alternative device for holding the separated coracoid bone transplant to the double cannula is shown at 45 in FIG. 16. The distal section of the spike in FIG. 16 is expandable to hold the device to the walls of the bores of the graft.

The sutures/wires holding the coracoid can now be removed. The exact positioning on the glenoid may be assisted by using a suitable instrument, such as the clamping device shown at 46 in FIGS. 17a and 17b. Once the transplant is in the correct position on the glenoid, Kirschner wires (31, FIG. 3) are driven into the glenoid through the cannulated devices holding the coracoid. The devices are now removed using the screwdriver 44, FIG. 15, or by releasing the spike 45.

The double cannula serves as a drill guide. With a cannulated drill 47a, FIG. 18, inserted over one of the Kirschner wires, a first hole is drilled into the glenoid. Leaving the first drill in position, the other drill 47b in FIG. 18, with the longer shaft, is used to drill a second hole over the second Kirschner wire.

Figure 19:

After removing the drills, cannulated bone screws 48, FIG. 19, are inserted over the K-wires into the coracoid graft and are screwed part-way into the glenoid using the cannulated device driver with a long shaft 49, FIG. 20, for use with the cannulated bone screws.

The K-wires can now be pulled out and the optional bone clamping device is removed. The bone screws 48 are drawn tight and the double cannula is withdrawn to conclude the procedure.

While the invention has been described with respect to a preferred embodiment, it will be appreciated that this is set forth merely for purposes of example, and that many other variations, modifications and applications of the invention may be made.

What is claimed is:

1. An arthroscopic procedure for transplanting a section of a first bone to a second bone using a double cannula, flexible wires or sutures, a cannulated device, K-wires and bone screws, wherein said procedure comprises: opening portals for the introduction of medical instruments; preparing the surfaces of said first bone and said second bone; drilling and threading two holes in said first bone at a fixed distance; passing said sutures or flexible wires through said holes; attaching said first bone by sutures or flexible wires to said double cannula; separating a section of said first bone to be transferred; positioning said section of said first bone on said second bone; inserting a cannulated device through said double cannula; introducing K-wires through said cannulated device; removing said cannulated device; drilling into said second bone over the K-wires; attaching said transferred section of said first bone onto said second bone using bone screws; removing the K-wires; tightening said bone screws; and removing said double cannula.

2. The procedure according to claim 1, wherein said double cannula comprises a distal end including two parallel tubes at a fixed distance from each other, and a proximal end serving as a handle.

3. The procedure according to claim 2, wherein the two tubes are formed with windows to enable observation of their interiors.

4. The procedure according to claim 1, wherein the arthroscopic procedure is for the treatment of an anterior shoulder instability, wherein said first bone is the coracoid, and the second bone is the glenoid.

5. The procedure according to claim 1, wherein said double cannula is used for maneuvering said separated section of said first bone onto said second bone.

6. The procedure according to claim 1, wherein said threading comprises implanting inserts within said holes.

7. The procedure according to claim 1, wherein a drill guide for producing two holes at a fixed distance from each other is used for producing said two holes in said first bone.

8. The procedure according to claim 1, wherein an osteotome is used for said separating a section of said first bone.

9. The procedure according to claim 8, wherein said osteotome comprises a curved distal end.

10. The procedure according to claim 1, further comprising dissecting tissue for freeing a passage to said second bone using a cannulator.

11. The procedure according to claim 1, wherein a cannulated bone drill is used for drilling said holes.

12. The procedure according to claim 1, wherein said bone screws are cannulated to be inserted over said K-wires.

13. An arthroscopic procedure for transplanting a section of a first bone to a second bone inside a human body, comprising preparing surfaces of the first and second bone, separating said section of first bone, maneuvering said section of the first bone onto the second bone without removing said section from the body, and attaching said section of first bone onto said second bone, wherein the arthroscopic procedure is for the treatment of an anterior shoulder instability, wherein said first bone is the coracoid, and the second bone is the glenoid, wherein a double cannula is used for said maneuvering of said separated section of said first bone onto said second bone.

14. The procedure according to claim 13, wherein said double cannula comprises a distal end including two parallel tubes at a fixed distance from each other, and a proximal end serving as a handle.

15. The procedure according to claim 13, wherein an osteotome is used for said separating a section of said first bone.

16. The procedure according to claim 13, wherein said preparing surfaces comprises drilling and threading two holes in said first bone.

17. The procedure according to claim 16, wherein a drill guide for producing two holes at a fixed distance from each other is used for producing said two holes in said first bone.

18. The procedure according to claim 16, wherein said threading comprises implanting inserts within said holes.

\* \* \* \* \*